(12) United States Patent
Liaw

(10) Patent No.: US 8,349,999 B2
(45) Date of Patent: Jan. 8, 2013

(54) PYRENE-CONTAINING NORBORNENE METHYLENE AMINE AND POLYMER THEREOF, AND METHOD FOR MANUFACTURING THE POLYMER

(75) Inventor: Der-Jang Liaw, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 115 days.

(21) Appl. No.: 12/801,113

(22) Filed: May 24, 2010

(65) Prior Publication Data

US 2011/0092666 A1    Apr. 21, 2011

(30) Foreign Application Priority Data

Oct. 15, 2009   (TW) .............................. 98134966 A

(51) Int. Cl.
*C08G 73/00*   (2006.01)

(52) U.S. Cl. ......................................... 528/422; 564/428
(58) Field of Classification Search .................. 528/422; 564/428

See application file for complete search history.

(56) References Cited

U.S. PATENT DOCUMENTS

2009/0023877 A1 * 1/2009 Liaw et al. .................... 526/259

* cited by examiner

*Primary Examiner* — Shane Fang
(74) *Attorney, Agent, or Firm* — Bacon & Thomas, PLLC

(57) ABSTRACT

The present invention discloses a pyrene-containing norbornene methylene amine which can be synthesized by 5-(amino methyl)bicycle[2.2.1]hept-2-ene (NBMA) and 1-bromopyrene. The pyrene-containing norbornene methylene amine can be used as a monomer for synthesizing a polymer containing pyrene side chain via Ring-Opening Metathesis Polymerization (ROMP). The polymer has good transmittance, optical and thermal properties.

13 Claims, 12 Drawing Sheets

PYRENE-CONTAINING NORBORNENE METHYLENE AMINE AND POLYMER THEREOF, AND METHOD FOR MANUFACTURING THE POLYMER

BACKGROUND OF THE INVENTION (1) Field of the Invention

The present invention relates to a norbornene methylene amine and polymer thereof, and more particularly relates to a norbornene methylene amine containing luminophore at the side chain and polymer thereof.

(2) Description of the Prior Art

Olefin metathesis reaction has received much attention in recent years as a new synthesis method of carbon-carbon bonds. With the development of various kinds of catalysts, metathesis polymerization of ring diene, non-ring diene and alkyne is increasingly important. Among them, norbornene derivative can be used for synthesizing polymers with a variety of function groups via Ring-Opening Metathesis Polymerization (ROMP), which becomes one of the important synthesis methods for polymer materials.

Polynorbornene and polymer thereof is a first commercial product via ring-opening metathesis polymerization and also one of the most important engineering plastics. Because of its good transmittance, impact resistance, wide range of temperature, good mechanical property and workability, it is widely used in rubber additives, lighting equipment, machinery, electronic parts, pipe fitting and food packaging. Moreover, its derivatives, such as acid and ester polymer, are even used as photoresist in electrical industry.

Organometallic catalysts has been used for metathesis polymerization for a period of time, but polymerization for the monomer with functional groups is sort of limited, and moisture or oxygen is also quite sensitive to the polymerization. For example, metal compounds like tungsten (W), titanium (Ti), molybdenum (Mo) and ruthenium (Ru) are commonly used as ring vinyl metathesis polymerization catalyst, and among them, Grubbs's catalyst has better stability and tolerance of water or oxygen and can even be polymerized in water. For example, $Cl_2Ru(CHPh)[P(C_6H_{11})_3]_2$ is very effective for ring vinyl metathesis polymerization, and rather stable in the air so that it can polymerize monomer with functional groups.

In order to get more kinds of polymer materials with excellent properties, ROMP of norbornene allyl derivatives with functional groups is worthy of further study.

SUMMARY OF THE INVENTION

An exemplary embodiment of the present invention provides a norbornene methylene amine polymer containing pyrene side chain, with good transmittance, good mechanical property and workability, thermal property, and strong fluorescence which can be applied to fluorescence and luminescence materials.

Other purposes and advantages of the present invention can be obtained from the technical features disclosed hereinafter.

In order to achieve one or part or all of the above-mentioned purposes or other purposes, the present invention provides a general formula (I) to represent pyrene-containing norbornene methylene amine polymer:

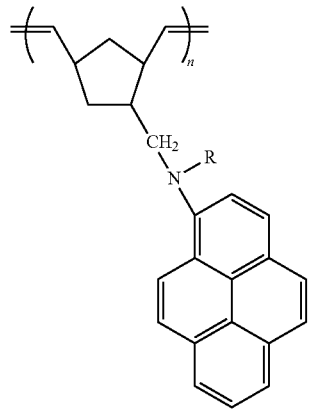

(I)

where R=H or

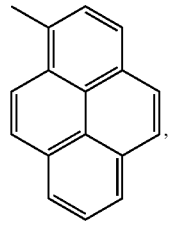

n is from 2 to 1000,
and a general formula (II) to represent pyrene-containing norbornene methylene amine:

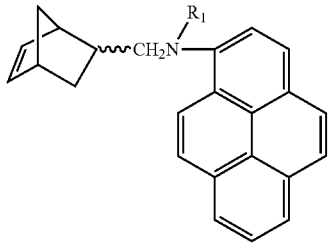

(II)

where R1=H or

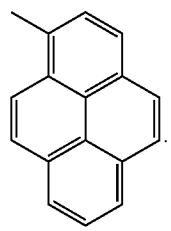 [SMILES: Cc1ccc2ccc3cccc4ccc1c2c34]

For manufacturing the above pyrene-containing norbornene methylene amine polymer, firstly, the pyrene-containing norbornene methylene amine in accordance with formula (II) is synthesized by means of norbornene methylene amine reacting with bromopyrene, then the pyrene-containing norbornene methylene amine polymer in accordance with formula (I) is synthesized by polymerizing the pyrene-containing norbornene methylene amine, and then hydrogenates the polymer. In an example, the above reaction is ring-opening metathesis polymerization (ROMP) which uses ruthenium (Ru) as catalyst and ethyl vinyl ether to terminate the reaction.

Norbornene methylene amine and Bromine pynene are dissolved in anhydrous toluene and heated to carry out refluxing. The liquid mixture obtained after refluxing is filtered, extracted and purified to get pyrene-containing norbornene methylene amine.

In an example, the pyrene-containing norbornene methylene amine includes disubstituted pyrene, and has weight percentage of elements as follows: carbon 90.89-91.74%, hydrogen 5.28-5.58% and nitrogen 2.52-2.67%.

In another example, the pyrene-containing norbornene methylene amine includes monosubstituted pyrene, and has weight percentage of elements as follows: carbon 88.56-89.13%, hydrogen 6.34-6.54% and nitrogen 4.21-4.33%.

The present embodiments use norbornene methylene amine and different mol 1-bromopyrene to synthesize NBEMPY or NBEDIPY and then use ROMP to synthesizing poly(NBEMPY) or poly(NBEDIPY). The polymer obtained after hydrogenation can be used as plastic material, bonding material, photosensitive material, luminescent material, fluorescent material or non-linear optical material, and applied for liquid crystal display, or flexible printed circuit board.

DESCRIPTION OF THE PREFERRED EMBODIMENTS

Figure 1:
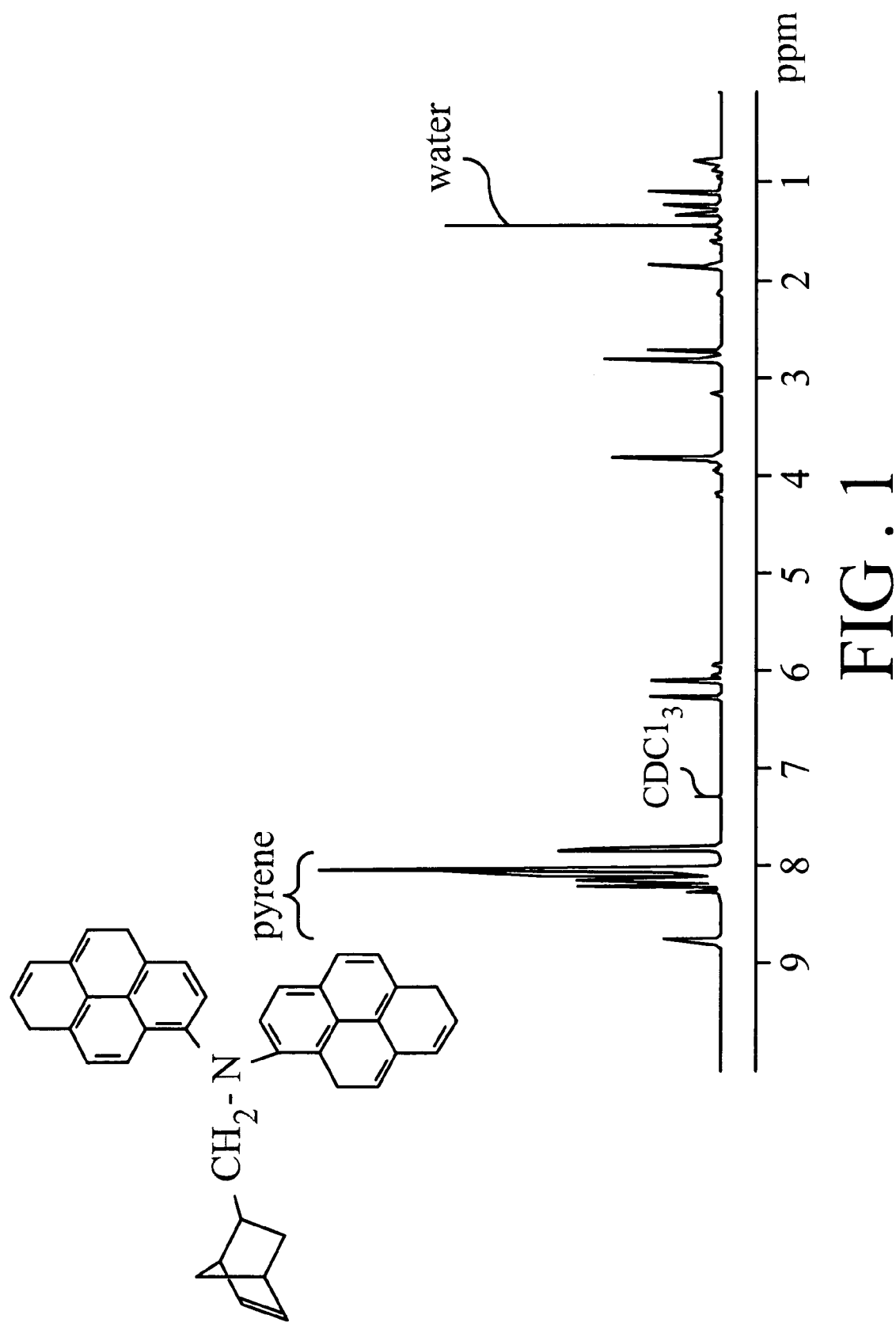
FIG. 1 is a $^1$H-NMR spectrum of NBEDIPY.

In the following detailed description of the preferred embodiments, reference is made to the accompanying drawings which form a part hereof, and in which is shown by way of illustration specific embodiments in which the invention may be practiced.

[1st Embodiment] The Synthesis of NBEDIPY

The present embodiment uses norbornene methylene amine (NBMA) and 1-bromopyrene to synthesize the disubstituted pyene-containing norbornene methylene amine (NBEDIPY) such as 5-(dipyrene amino methyl)-bicyclo[2,2,1]hept-2-ene. The NBEDIPY is used for synthesizing poly(NBEDIPY) with disubstituted pyene at the side chain via Ring-Opening Metathesis Polymerization (ROMP). The NBMA is generated by means of cyclopentadiene reacting with allyl amine. 1-bromopyrene is generated by means of pyrene reacting with N-bromosuccinimide (NBS). Cyclopentadiene is generated by means of pyrolysising dicyclopentadiene reacting with hydroquinone. Here are detailed steps:

1. Reaction formula (a1) and steps of synthesizing cyclopentadiene are as follows:
Perform a thermal pyrolysis process of 1 mol dicyclopentadiene with 0.5 g hydroquinone under normal pressure at 180° C. and distill the product of the thermal pyrolysis to get cyclopentadiene.

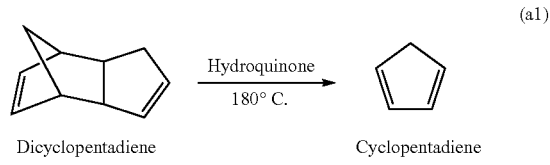 [SMILES: C1=CC2C3C=CC(C3)C2C1 ; C1=CCC=C1]

Dicyclopentadiene        Cyclopentadiene

2. Reaction formula (a2) and steps of synthesizing NBMA are as follows:
(1). Put 50 g cyclopentadiene, allyl amine having the same equivalent number as cyclopentadiene, and 0.1 g hydroquinone to react in a high pressure reactor for 8 hours at 180□;
(2). Get rid of extra cyclopentadiene and allyl derivatives in the solution obtained by step (1) by a rotary thickener; and
(3). Distill the solution obtained in step (2) to get NBMA under 54-56□/11 mmHg.

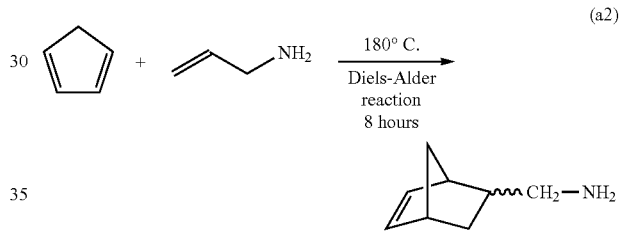

Cyclopentadiene    Allyl amine    norbornene methylene amine

3. Reaction formula (a3) and steps of synthesizing 1-bromopyrene are as follows:
(1). add 0.0445 mol pyrene and 45 mL anhydrous N,N-dimethyl formamide in a 250 mL reaction bottle, and stir them by magnetic stirrer until completely dissolved;
(2). dissolve 0.0445 mol n-bromosuccinimide in 40 mL anhydrous N,N-dimethyl formamide, and drop the solution to the above reaction bottle in a speed of 1 drop per second through an isobaric funnel;
(3). wrap the whole reaction equipment by a black plastic bag in a room temperature for 12 hours to avoid exposure to light;
(4). precipitate in water after complete reaction; and
(5). recrystallize and purify the crude product by n-hexane to get 1-bromopyrene.

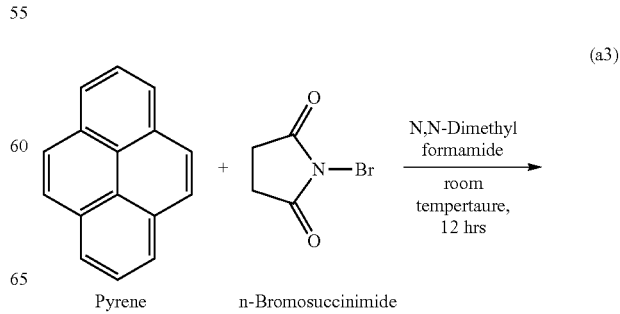

Pyrene      n-Bromosuccinimide

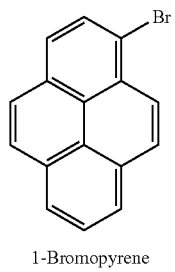

1-Bromopyrene

4. Reaction formula (a4) and steps of synthesizing NBEDIPY are as follows:

(1). Add 10 mmol 1-bromopyrene, 0.1 mmol palladium(II) acetate, 7.5 mmol sodium tert-butoxide, 0.2 mmol tri-tert-butylphosphine, 4.3 mmol NBMA and 50 mL anhydrous toluene in a 250 mL reaction bottle and stir them by magnet evenly;

(2). Reflux at 110□ and monitor the process by thin layer chromatography (TLC) until complete reaction.

(3). After filtering the liquid mixture obtained in step (2), remove toluene by rotary evaporator, extract by water and dichloromethane to get lower phase solution, and remove solvent to get crude solid product by rotary evaporator.

(4). Purify above crude solid product by column chromatography with a ratio of dichloromethane: n-hexane=1:3 to get NBEDIPY, a light green fluorescence solid, whose melting point is 155□.

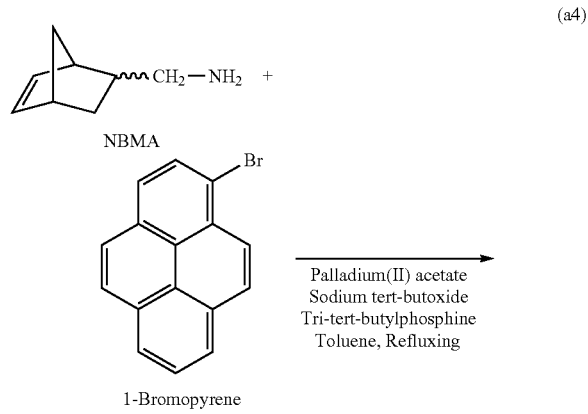

Figure 2:
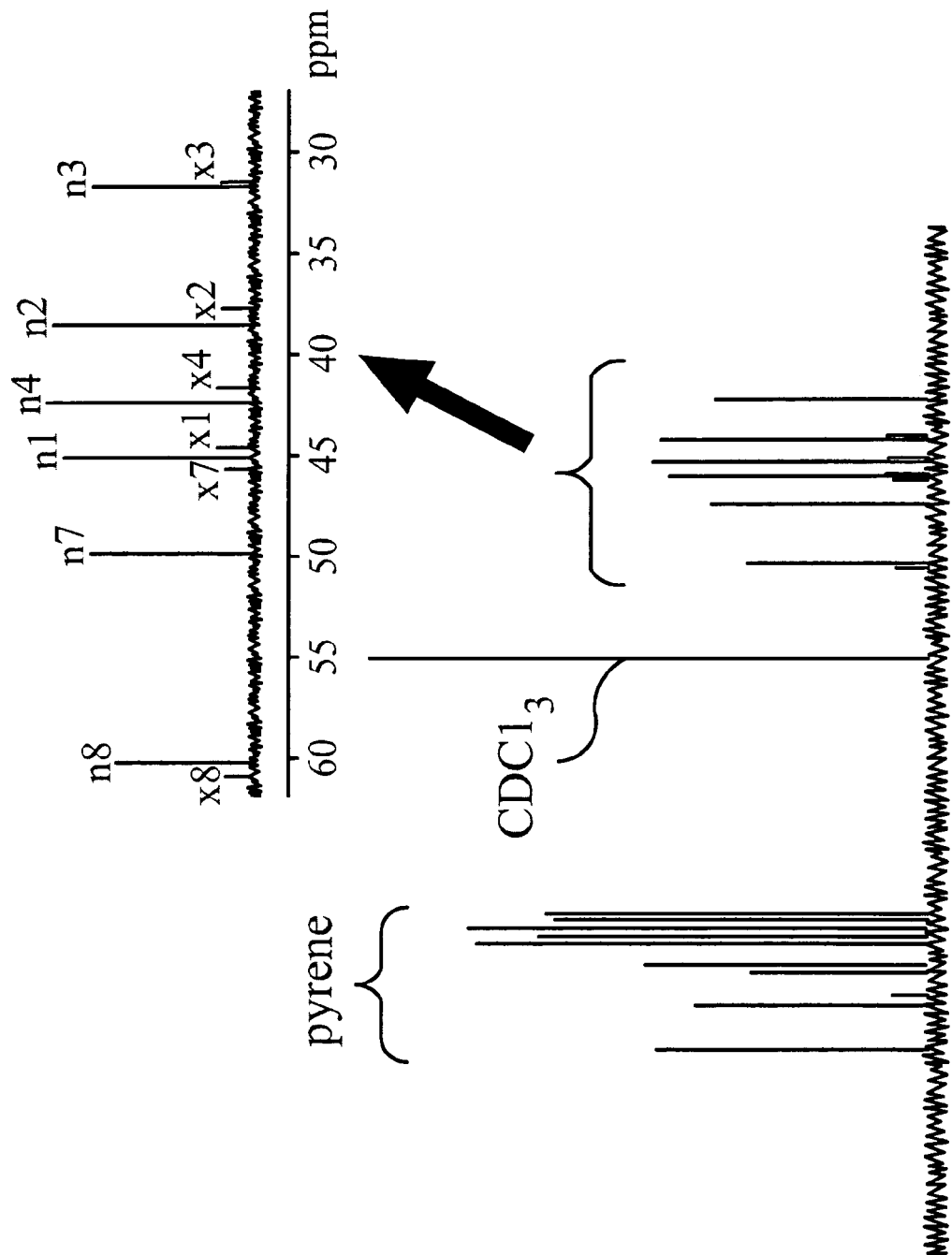
FIG. 2 is a $^{13}$C NMR spectrum of NBEDIPY.
Figure 3:
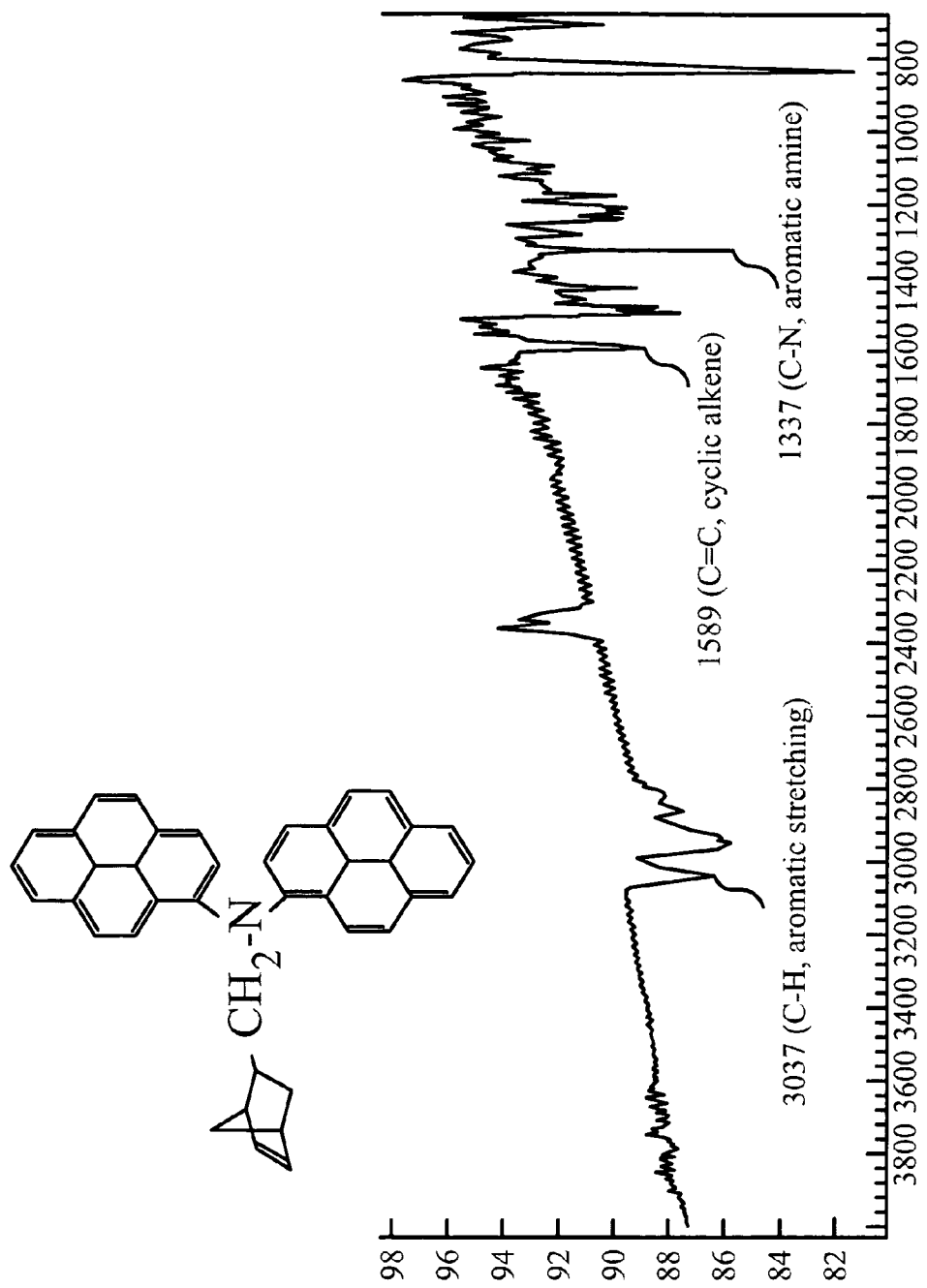
FIG. 3 is a FTIR spectrum of Poly(NBEDIPY).

Meanwhile, NBEDIPY is identified by $^1$H-NMR (FIG. 1) and $^{13}$C-NMR (FIG. 2) of Nuclear magnetic resonance spectrum (NMR spectrum), Fourier transform infrared spectrum (FTIR) and elemental analysis (FIG. 3).

FIG. 1 is a $^1$H-NMR spectrum of NBEDIPY (solvent: CDCl$_3$). It displays signals as follows: δ (ppm)=0.89 (H$_{n3}$), 0.92 (H$_{n3}$), 1.20 (H$_{n7}$), 1.22 (H$_{x3}$), 1.35 (H$_{n7}$), 1.62 (H$_{x7}$), 1.70 (H$_{x7}$), 1.97 (H$_{x3}$), 2.22 (H$_{x2}$), 2.8 (H$_{n4}$), 2.83-2.90 (H$_{x4}$, H$_{n1}$, H$_{n2}$), 3.22 (H$_{x1}$), 3.82-3.95 (H$_{n8}$, 2H), 4.05 (H$_{x8}$), 4.20 (H$_{x8}$), 5.92 (H$_{x6}$), 6.04 (H$_{x5}$), 6.10 (H$_{n6}$), 6.26 (H$_{n5}$), 7.75-8.75 (H$_9$, 18H).

FIG. 2 is a $^{13}$C-NMR spectrum of NBEDIPY (solvent: CDCl$_3$). It displays signals as follows: δ (ppm)=31.49 (C$_{x3}$), 31.62 (C$_{n3}$), 37.3 (C$_{x2}$), 38.54 (C$_{n2}$), 41.66 (C$_{x4}$), 42.37 (C$_{n4}$), 44.62 (C$_{x1}$), 45.14 (C$_{n1}$), 45.61 (C$_{x7}$), 49.92 (C$_{n7}$), 60.28 (C$_{n8}$), 60.93 (C$_{x8}$), 122.38-146.00 (C$_9$), 132.61 (C$_{n1}$), 136.59 (C$_{x1}$), 136.76 (C$_{x2}$), 138.17 (C$_{n2}$).

FIG. 3 is a FTIR spectrum of NBEDIPY (KBr pellet, cm$^{-1}$): 1337 (C—N, aromatic amine), 1589 (C═C, cyclic alkene), 3037 (C—H, aromatic stretching).

Elemental analysis: theoretical values of C$_{40}$H$_{29}$N are Carbon (C), 91.74%; Hydrogen (H), 5.58%; Nitrogen (N), 2.67%, and measured values are C, 90.89%; H, 5.28%; N, 2.52%. According to above values, the ranges of element weight percentage of NBEDIPY are C, 90.89-91.74%; H, 5.28-5.58%; and N, 2-2.67%.

5. Reaction formula (a5) and steps of synthesizing NBEDIPY via Ring-Opening Metathesis Polymerization are as follows:

(1). Dissolve 0.911 mmol NBEDIPY in 3 mL dichloromethane in an ultra-high vacuum reaction bottle, and connect to a high vacuum system, repeat the cycle of freezing-vacuum-unfreezing for 3 times, extract the air in the bottle by vacuum pump and then seal the bottle by flame gun or gas spray gun;

(2). Dissolve 7.5 mg ruthenium metal catalyst, for example, Grubbs's catalyst, in 0.2 mg dichloromethane in a glove box filled with Argon and inject the solution into the reaction bottle by syringe;

(3). Perform reaction at 35□ for 2 hours after adding catalyst;

(4). Add 0.1 mL ethyl vinyl ether to terminate polymerization, precipitate the solution in 500 mL methanol filled with nitrogen, take out and dry the polymer; and (5). Dissolve the polymer in tetrahydrofuran (THF), then precipitate it in methanol, repeat 3 times, then dissolve it in benzene, freeze and dry it in room temperature to get Poly (NBEDIPY).

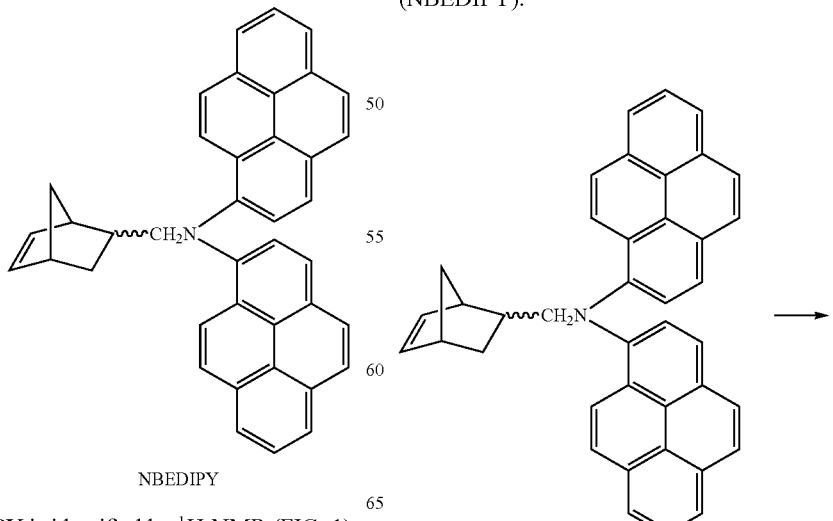

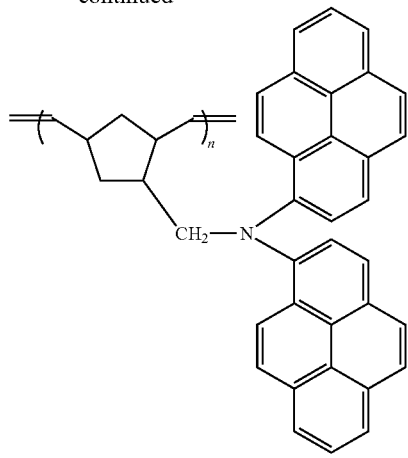

Figure 4:
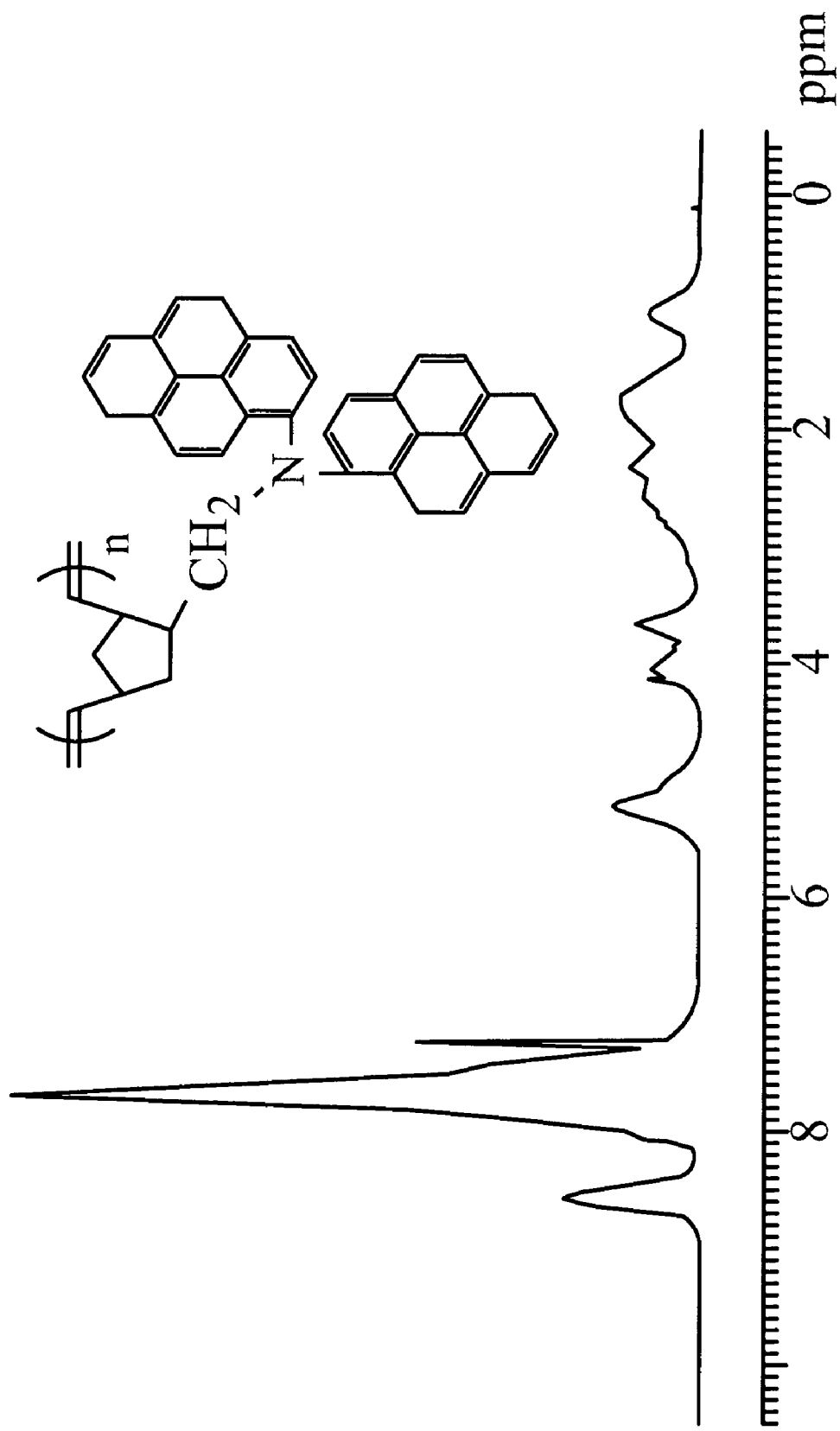
FIG. 4 is a $^1$H-NMR spectrum of Poly(NBEDIPY).

FIG. 4 is a $^1$H-NMR spectrum of Poly(NBEDIPY) (solvent: CDCl$_3$). It displays signals as follows: δ (ppm)=1.04 (H$_3$), 1.29-2.36 (H$_1$, H$_2$, H$_3$, H$_4$, H$_7$), 3.68-4.18 (H$_8$), 5.24 (H$_5$, H$_6$), 7.27-8.59 (H$_9$).

Figure 5:
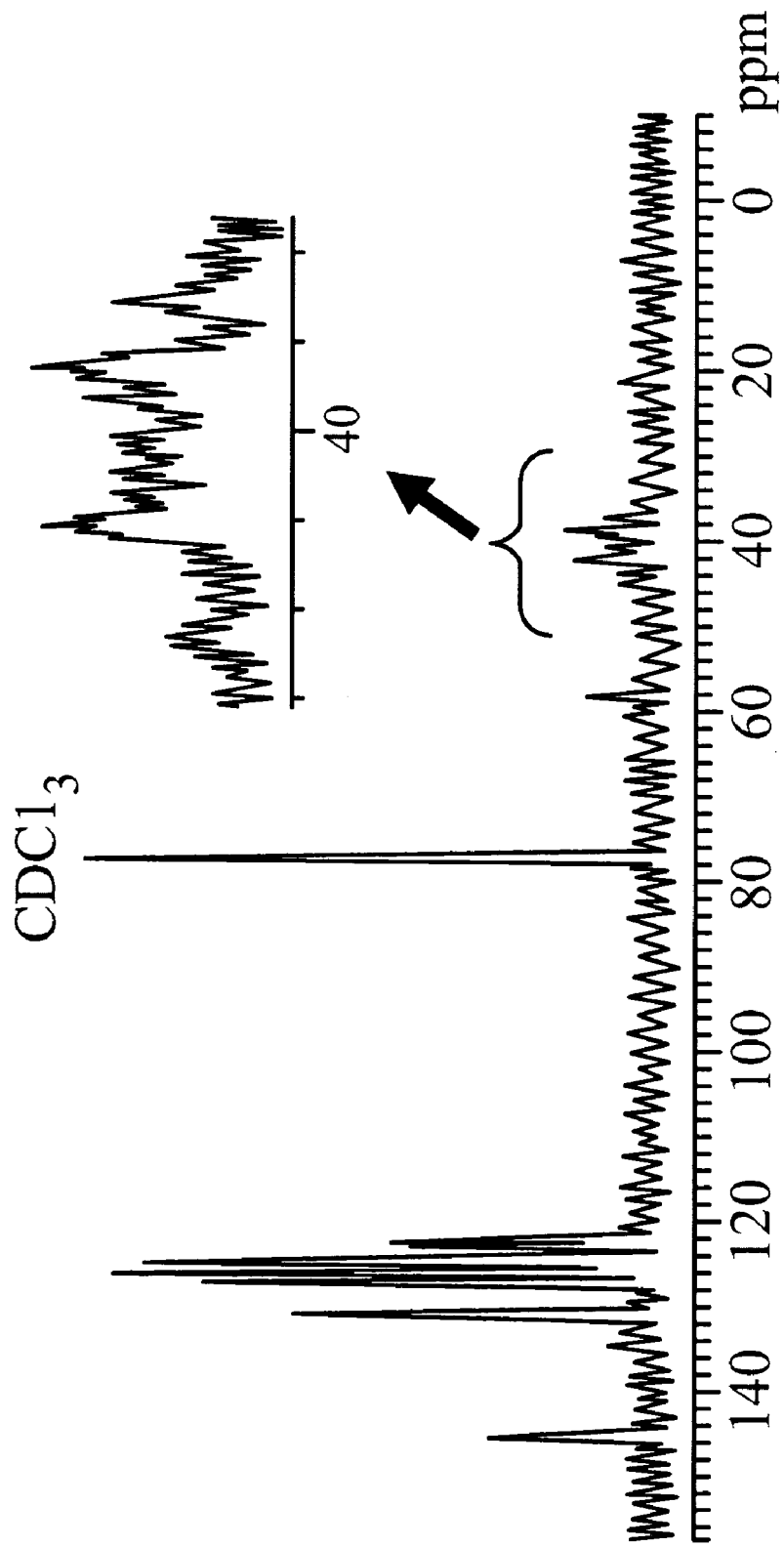
FIG. 5 is a $^{13}$C-NMR spectrum of Poly(NBEDIPY).

FIG. 5 is a $^{13}$C-NMR spectrum of Poly(NBEDIPY) (solvent: CDCl$_3$). It displays signals as follows: δ (ppm)=36.97 (C$_2$), 38.43 (C$_4$), 40.36 (C$_3$, C$_7$), 40.90 (C$_1$), 57.93 (C$_8$), 122.33-127.15 (C$_5$, C$_6$, C$_9$).

Figure 6A:
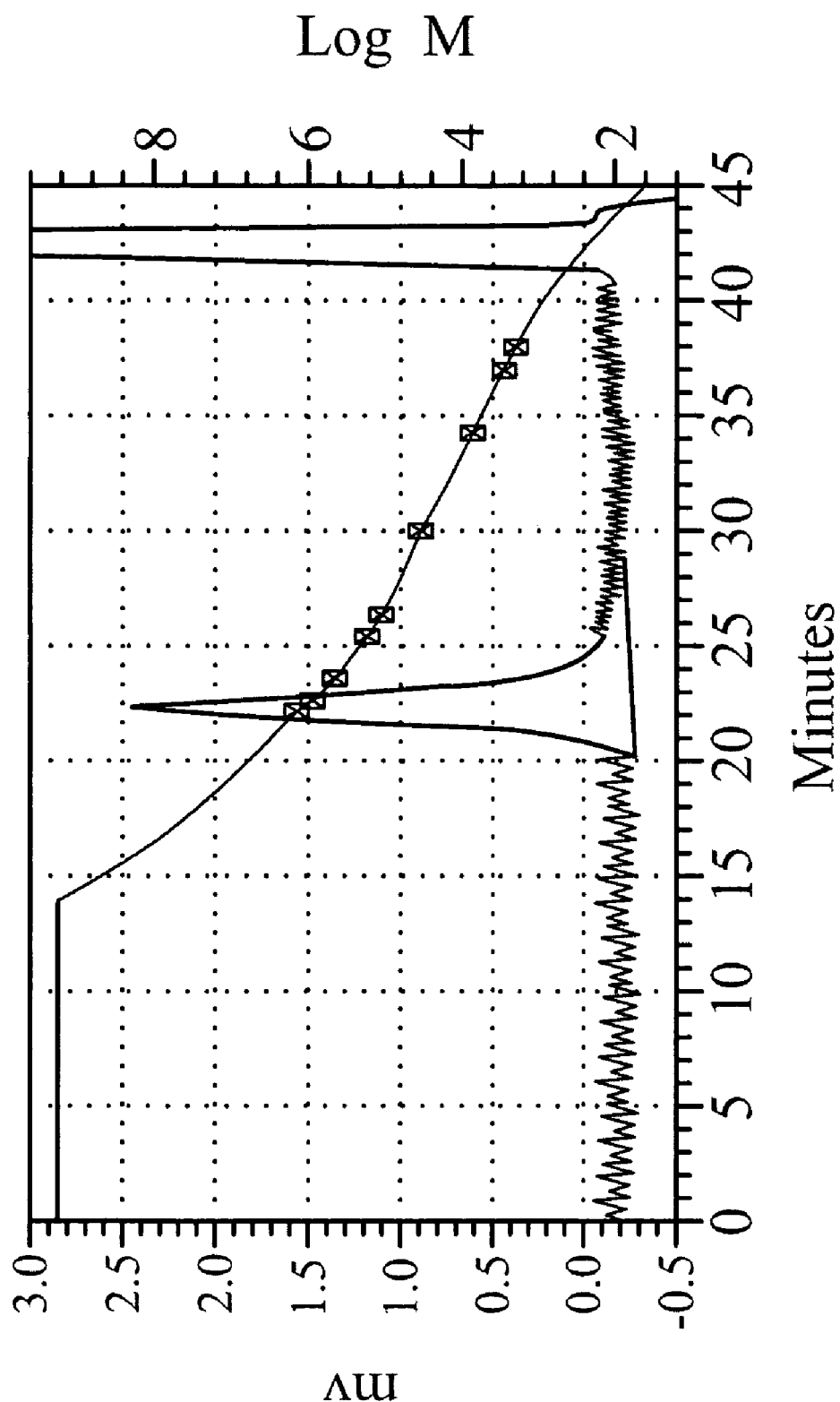
FIG. 6A is a graph of a gel permeation chromatography (GPC) trace of Poly(NBEDIPY).
Figure 6B:
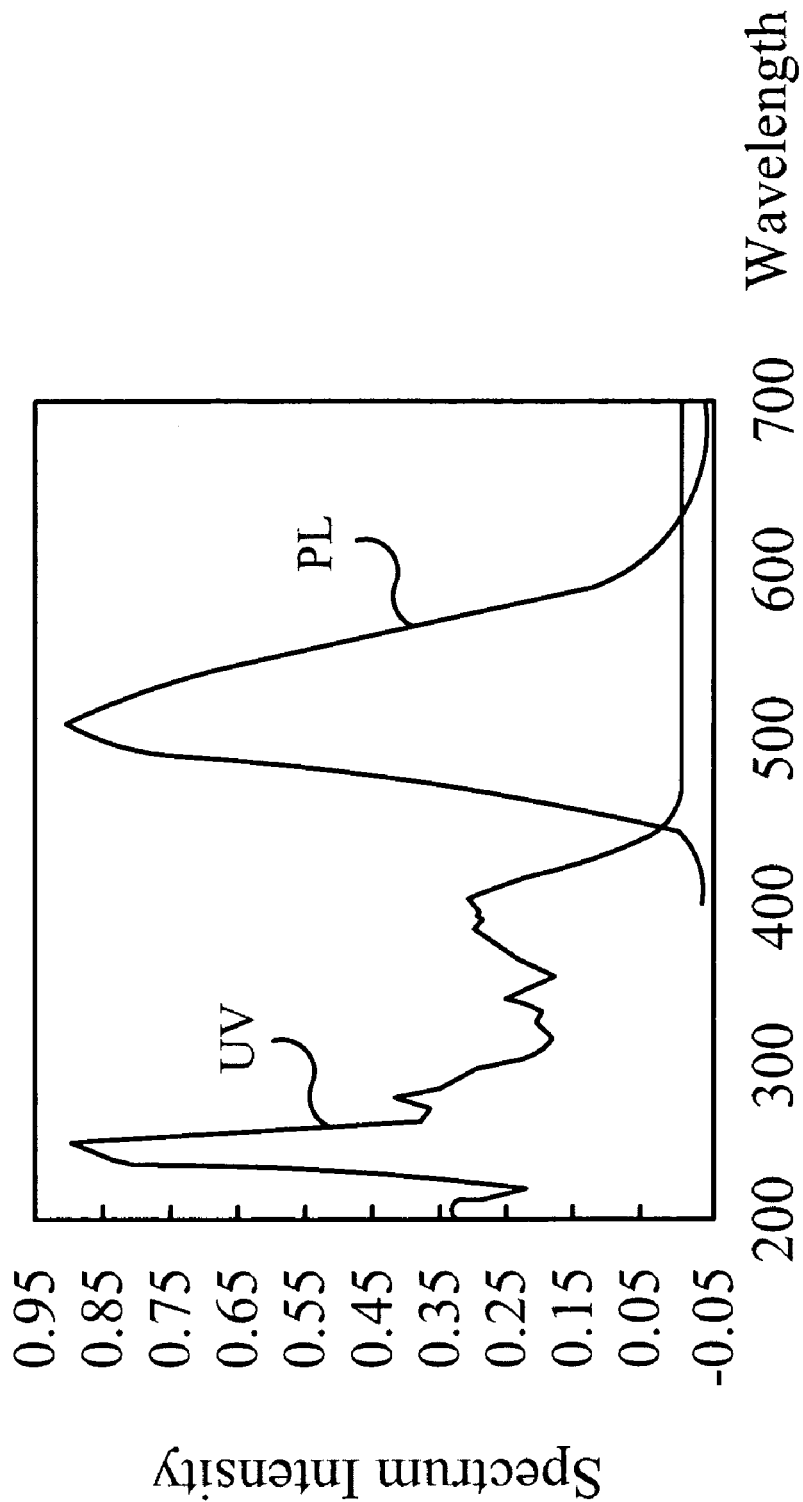
FIG. 6B is an UV and photoluminescence absorption spectrum of Poly(NBEDIPY).

Referring to FIG. 6A, the GPC trace shows Poly(NBEDIPY) has a number-average molecular weight (Mn) of about 515000 and a weight-average molecular (Mw) of about 855000. The polydispersity (Mw/Mn) is about 1.66. Referring to FIG. 6B, the maximum UV absorption wavelength of Poly(NBEDIPY) in THF is 394 nm and the maximum photoluminescence (PL) absorption wavelength is 504 nm; in solid state, the maximum UV absorption wavelength is 400 and 386 nm, and the maximum PL absorption wavelength is 498 nm.

Figure 7A:
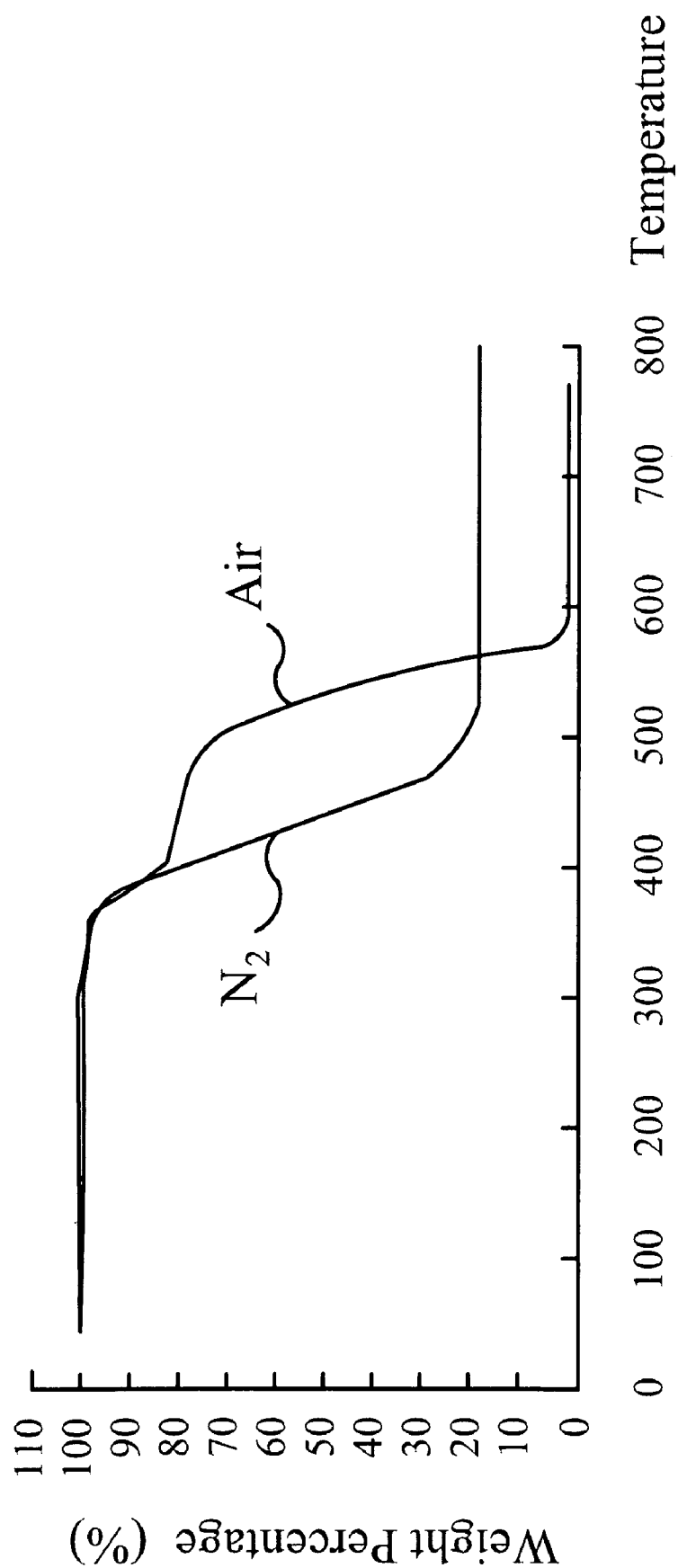
FIG. 7A is a diagram showing weight percentage of Poly(NBEDIPY) measured in the air and nitrogen atmosphere by TGA.
Figure 7B:
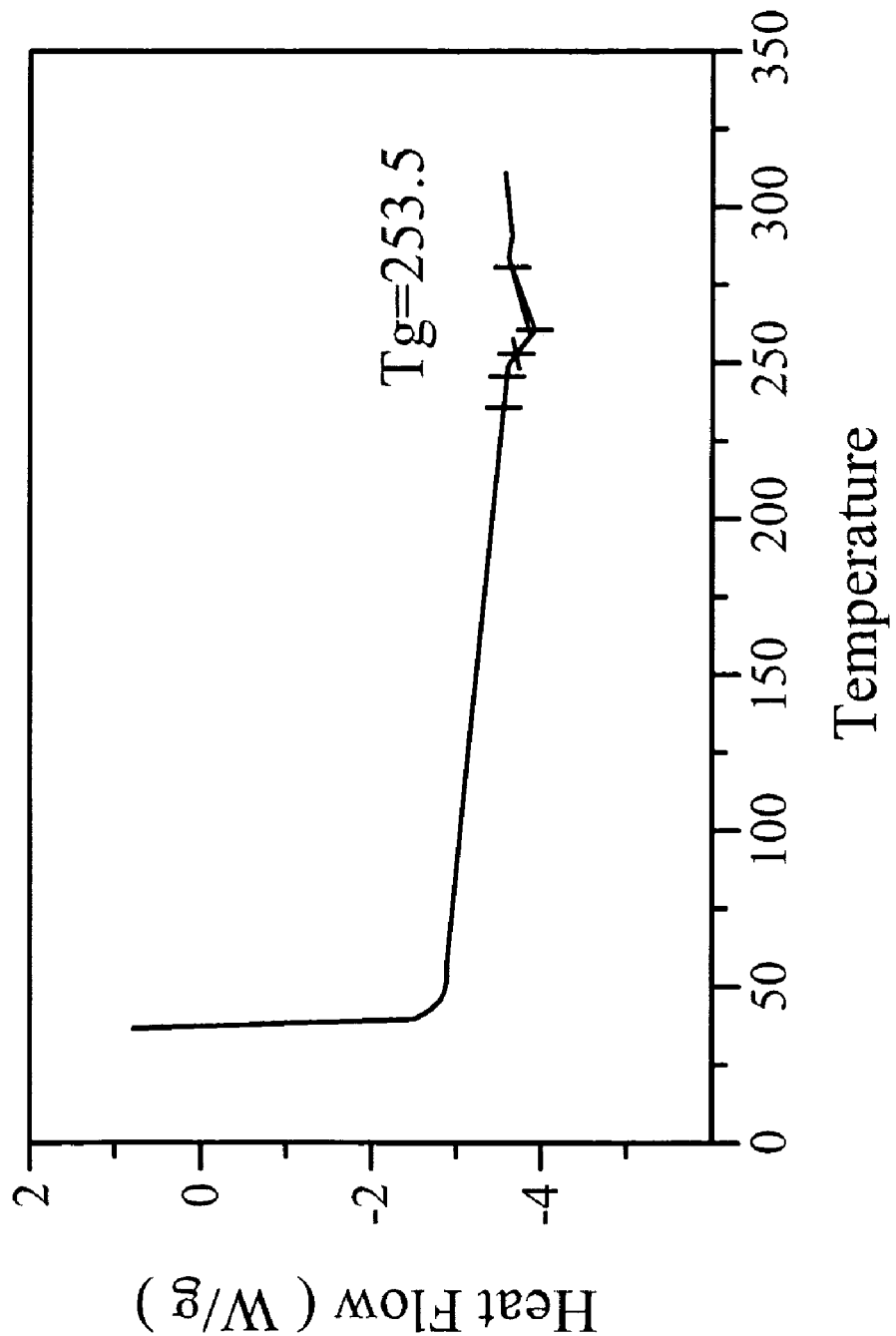
FIG. 7B is a differential scanning calorimeter (DSC) diagram of Poly(NBEDIPY).

Referring to FIG. 7A, TGA is used to measure Poly(NBEDIPY). In the air, its 10% thermal pyrolysis temperature is 389□, while in nitrogen (N$_2$), its 10% thermal pyrolysis temperature is 398□; meanwhile, its glass transition temperature is measured 253□ with a nitrogen flow of 10 c.c./min. Referring to FIG. 7B, the glass transition temperatures (Tg) of Poly(NBEDIPY) were 253.5□ determined from the DSC curves.

Figure 8:
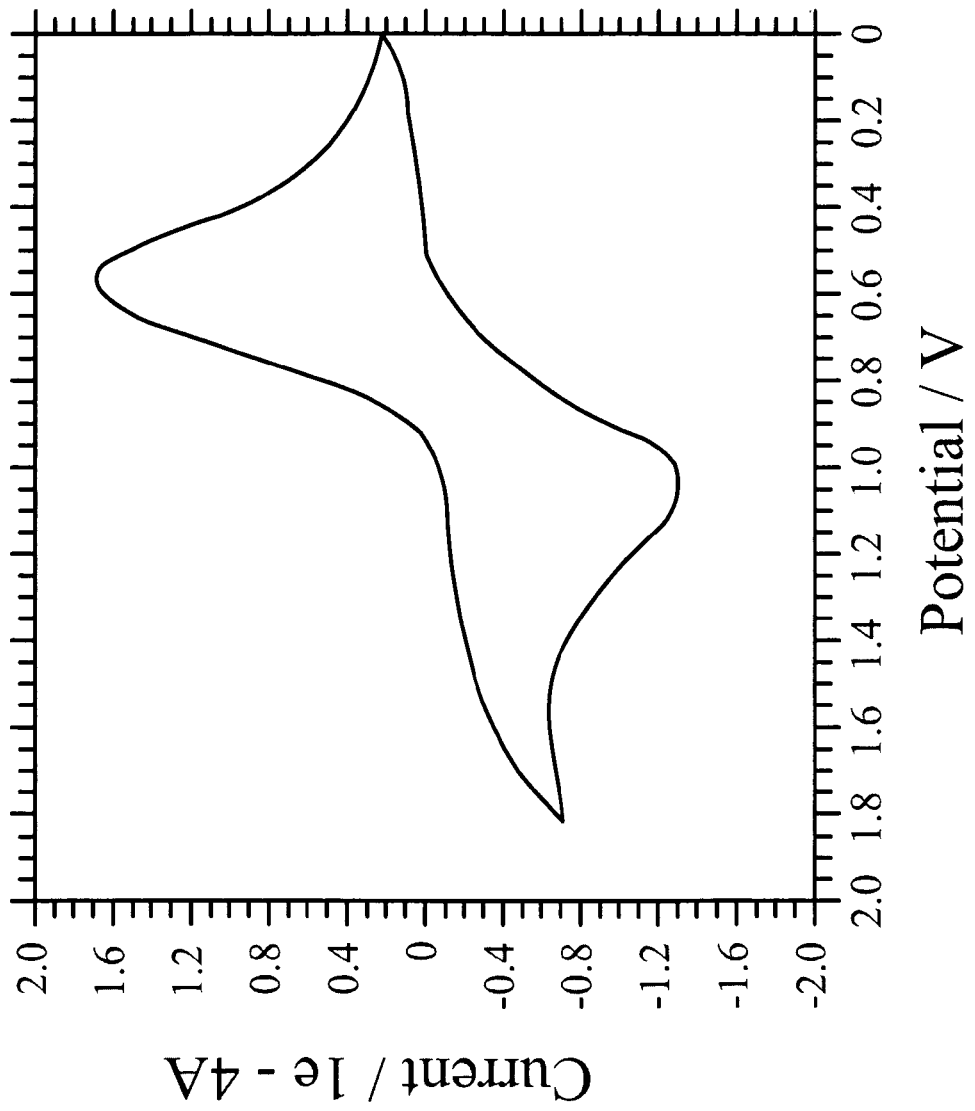
FIG. 8 is a relationship graph of current and voltage of Poly(NBEDIPY).

FIG. 8 shows electrochemical property of Poly(NBEDIPY) measured by cyclic voltammetry (CV). In the near-vacuum environment, its oxidation voltage is 4.8 (eV) after adding ferrocene and ferrocenenium, so that we can calculate the energy order of the highest occupied molecular orbital (HOMO) of the conjugated polymer. Thus, the lowest unoccupied molecular orbital (LUMO) can be calculated by the below formula: LUMO=HOMO+Eg. In THF, HOMO and LUMO of Poly(NBEDIPY) are calculated −5.1 ev and −2.37 eV.

6. Steps of hydrogenation of Poly(NBEDIPY) are as follows:

(1). Put 1.07 mmol Poly(NBEDIPY), 1.45 g (7.8 mmol) p-toluenesulfon hydrazide, 0.03 g 2,6-di-tert-butyl-4-methylphenol and 20 mL xylene in a reaction bottle, repeat the cycle of freezing-vacuum-sealing tube-unfreezing 4 times;

(2). Perform the reaction in 120□ for 12 hours; and (3). Cool to room temperature, and pour the solution into a large quantity of methanol to get hydrogenated poly(NBEDIPY), denoted as Poly(HNBEDIPY).

[2nd Embodiment] Synthesis of Poly(NBEMPY)

The 2nd embodiment uses NBMA and 1-bromopyrene with different mol from the 1st embodiment to synthesize monosubstituted pyene-containing norbornene methylene amine (NBEMPY) such as 5-(pyrene amino methyl)-bicyclo[2,2,1]hept-2-ene, and then synthesize poly(NBEMPY) via ROMP, where NBMA is generated based on reaction formula (a2) and cyclopentadiene is generated based on reaction formula (a1), which will not be described in the present embodiment. Other steps are illustrated hereinafter:

1. Reaction formula (a6) and steps of synthesizing NBEMPY are as follows:

(1). Add 10 mmol bromopyrene, 0.1 mmol palladium(II) acetate, 7.5 mmol sodium tert-butoxide, 0.2 mL tri-tert-butylphosphine, 11.5 mmol NBMA and 50 mL toluene in a 500 mL reaction bottle, and stir them evenly by magnet.

(2). Reflux at 110□ and monitor the process by thin layer chromatography (TLC) until complete reaction.

(3). After filtering the liquid mixture obtained by step (2), remove toluene by rotary evaporator, extract the liquid mixture by water and dichloromethane to get lower phase solution, and then remove solvent to get crude solid product by rotary evaporator.

(4). Purify above crude solid product by column chromatography with ratio of dichloromethane: n-hexane=1:3 to get NBMPYA, a yellow solid, whose melting point is 104□.

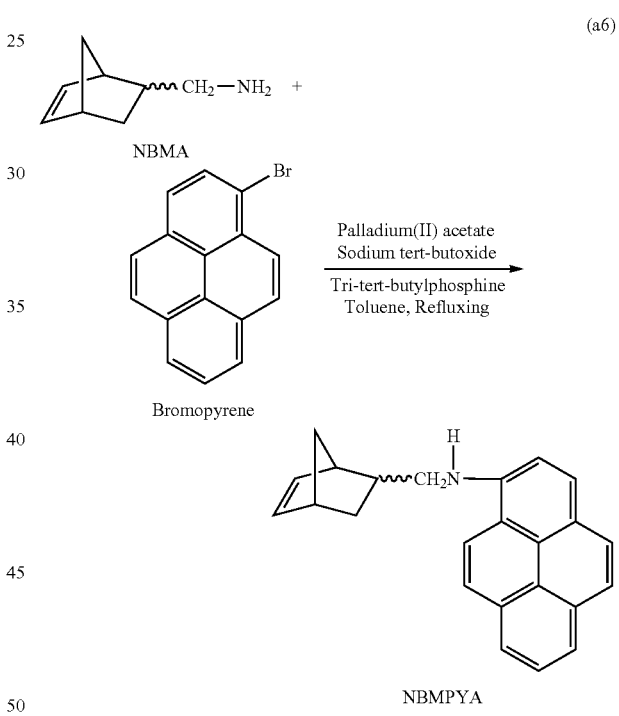

(a6)

2. Synthesize Poly(NBEMPY) via Ring-Opening Metathesis Polymerization based on reaction formula (a7):

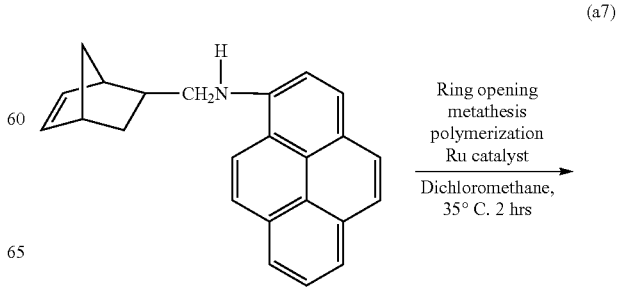

(a7)

-continued

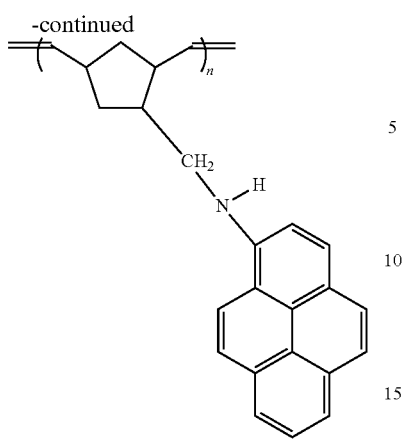

Except using NBEMPY as the monomer, other steps in reaction formula (a7) are same as Poly(NBEDIPY).

3. Hydrogenation of Poly(NBEMPY):

Except using Poly(NBEMPY) as polymer, other steps are same as hydrogenation of Poly(NBEDIPY).

Meanwhile, NBEMPY is identified by $^1$H-NMR (FIG. 8) and $^{13}$C-NMR (FIG. 9) of nuclear magnetic resonance spectrum (NMR spectrum), Fourier transform infrared (FTIR) and elemental analysis.

FTIR (KBr pellet, cm$^{-1}$): 3422 cm$^{-1}$ (N—H), 1279 cm$^{-1}$ (C—N stretch, aromatic), 1601 cm$^{-1}$ (C=C, pyrene) and 1468 cm$^{-1}$ (C=C, norbornene).

Elemental analysis: theoretical values of $C_{24}H_{21}N$ are C, 89.13%; H, 6.54%; N, 4.33% and measured values are C, 88.56%; H, 6.34%; N, 4.21%. According to above values, the ranges of element percentage of NBEMPY are C, 88.56-89.13%; H, 6.34-6.54% and N, 4.21-4.33%.

Figure 9:
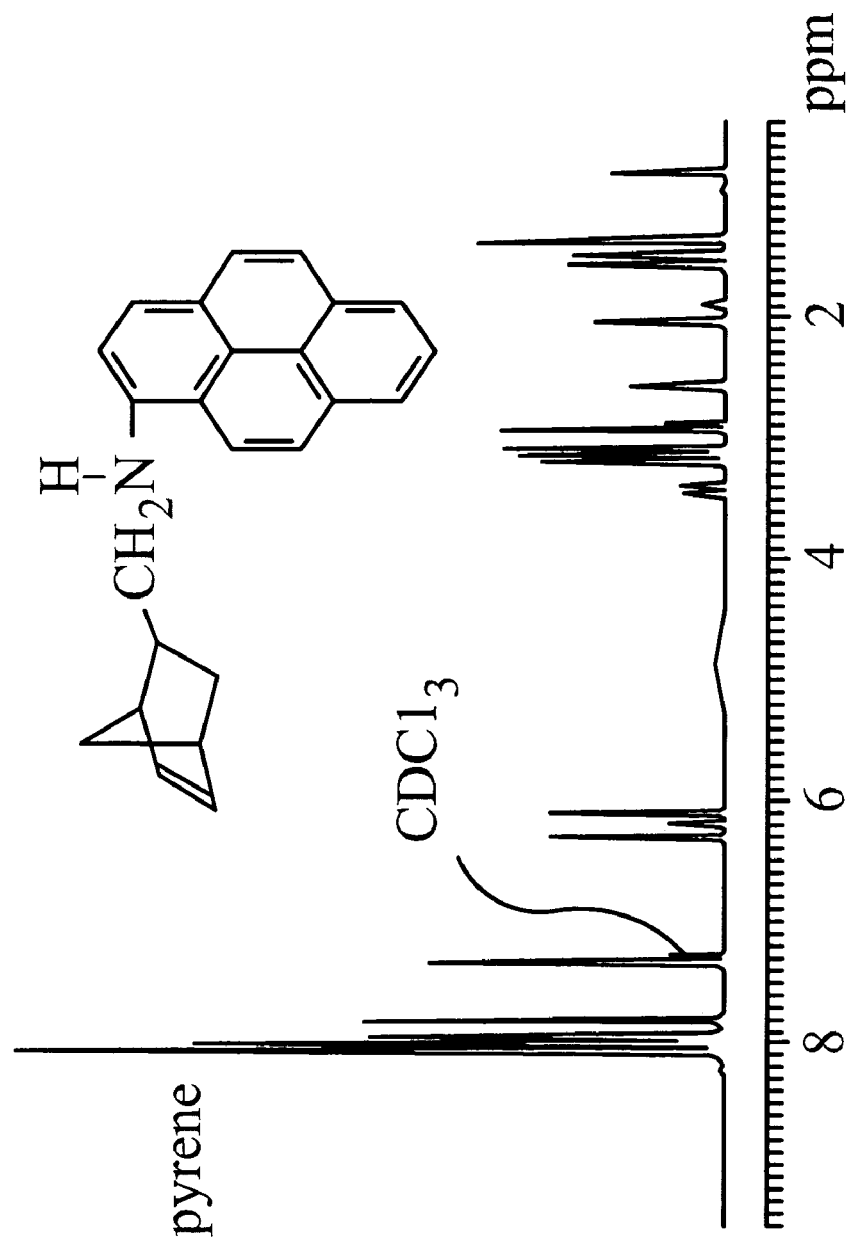
FIG. 9 is a $^1$H-NMR spectrum of NBEMPY.

FIG. 9 is a $^1$H-NMR spectrum of NBEMPY (solvent: CDCl$_3$). It displays signals as follows: δ (ppm)=0.79-0.82 ($H_{n3n}$; 1H), 1.34-1.38 ($H_{x3n}$; 1H), 1.36-1.38 ($H_{n7a}$; 1H), 1.47-1.51 ($H_{x3x}$, $H_{x7a}$, $H_{x7s}$; 3H), 1.57-1.59 ($H_{n7s}$; 1H), 1.87-1.92 ($H_{x2}$; 1H), 2.02-2.07 ($H_{n3x}$, 1H), 2.54-2.60 ($H_{n2}$; 1H), 2.89 ($H_{x1}$; 1H), 2.94 ($H_{n4}$ and $H_{x4}$; 2H), 3.11-3.22 ($H_{n8}$; 2H), 3.36-3.49 ($H_{x8}$; 2H), 4.70-4.90 ($H_9$; 1H), 6.10 ($H_{n6}$; 1H), 6.20 ($H_{x5}$ and $H_{x6}$; 2H), 6.29-6.30 ($H_{n5}$; 1H), 7.31-8.07 ($H_{10}$; 9H).

Figure 10:
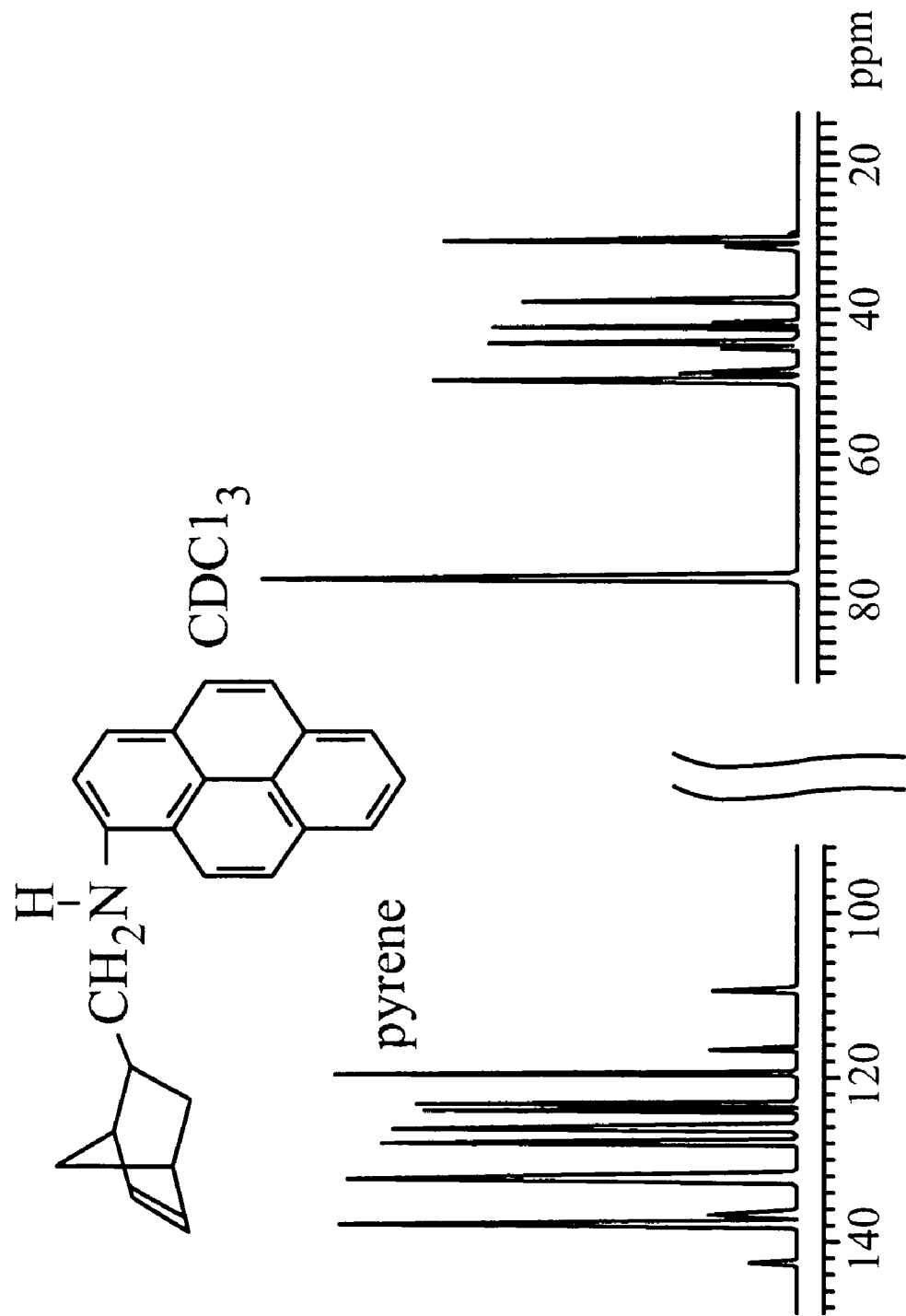
FIG. 10 is a $^{13}$C NMR spectrum of NBEMPY.

FIG. 10 is a $^{13}$C-NMR spectrum of NBEMPY (solvent: CDCl$_3$). It displays signals as follows: δ (ppm)=30.49 ($C_{n3}$), 31.32 ($C_{x3}$), 38.77 ($C_{n2}$), 39.01 ($C_{x2}$), 41.71 ($C_{x4}$), 42.41 ($C_{n4}$), 44.42 ($C_{n1}$), 44.61 ($C_{x1}$), 45.30 ($C_{x7}$), 48.63 ($C_{n8}$), 49.62 ($C_{n7}$), 49.96 ($C_{x8}$), 132.40 ($C_{n6}$), 136.35 ($C_{x6}$), 136.83 ($C_{x5}$), 137.8 ($C_{n5}$), (108.92-142.61) ($C_9$).

NBEMPY and NBEDIPY in the above embodiments can be hydrogenated to synthesize polymers with good transmittance, optical and thermal properties, good mechanical property and workability, and strong florescence. It can be used as high-performance engineering plastics, photographic material, luminescent material, adhesive, fluorescent material or nonlinear optical material for electrical devices like flexible print circuit board (PCB) and liquid crystal display (LCD) in semiconductor and precision machinery industry.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope and the appended claims which are to be accorded with the broadest interpretation so as to encompass all such modifications and similar structures. Furthermore, the abstract and title are used to facilitate searching rather than limit scope of the present invention.

What is claimed is:

1. A pyrene-containing norbornene methylene amine polymer comprising a formula (I) as:

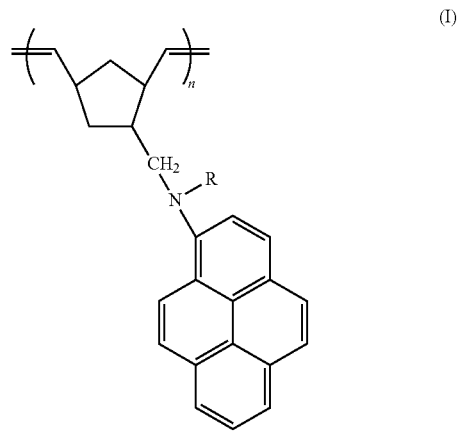

wherein R=H or

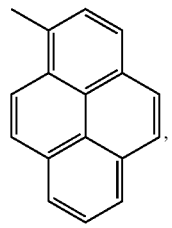 [SMILES: Cc1ccc2ccc3cccc4ccc1c2c34]

and n is from 2 to 1000.

2. A pyrene-containing norbornene methylene amine comprising a formula (II) as:

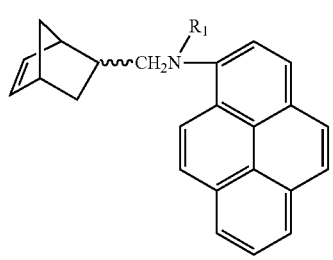

wherein, R1=H or

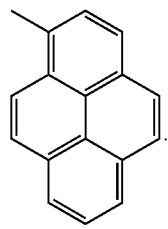 [SMILES: Cc1ccc2ccc3cccc4ccc1c2c34]

3. A method for manufacturing a pyrene-containing norbornene methylene amine polymer, comprising steps of:

synthesizing pyrene-containing norbornene methylene amine in accordance with formula (II)

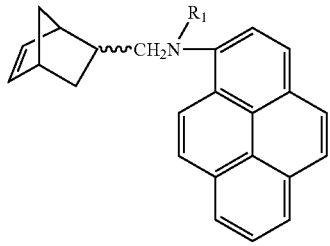 (II)

wherein, R1=H or

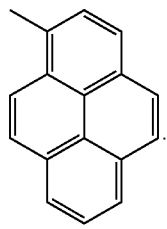 [SMILES: Cc1ccc2ccc3cccc4ccc1c2c34]

by norbornene methylene amine reacting with bromopyrene; and polymerizing the pyrene-containing norbornene methylene amine to synthesize pyrene-containing norbornene methylene amine polymer in accordance with formula (I) of claim 1.

4. The method for manufacturing the polymer of claim 3, further comprising a step of: hydrogenating the pyrene-containing norbornene methylene amine polymer.

5. The method for manufacturing the polymer of claim 3, wherein the bromopyrene is 1-bromopyrene.

6. The method for manufacturing the polymer of claim 3, wherein the norbornene methylene amine and the bromopyrene are dissolved in anhydrous toluene and heated for refluxing.

7. The method for manufacturing the polymer of claim 6, wherein a liquid mixture obtained by the refluxing is filtered, extracted and purified to get the pyrene-containing norbornene methylene amine.

8. The method for manufacturing the polymer of claim 7, wherein the pyrene-containing norbornene methylene amine comprises disubstituted pyrene, and consists of carbon, hydrogen and nitrogen elements, has three measured values and an allowable error by means of element analysis, wherein the three measured values are element weight percentage of carbon 90.89-91.74%; hydrogen 5.28-5.58%; and nitrogen 2.52-2.67%, the allowable error is weight percentage of 0-1.31%.

9. The method for manufacturing the polymer of claim 7, wherein the pyrene-containing norbornene methylene amine comprises monosubstituted pyrene, and consists of carbon, hydrogen and nitrogen elements has three measured values and an allowable error by means of element analysis, wherein the three measured values are element weight percentage of carbon 88.56-89.13%; hydrogen 6.34-6.54%; and nitrogen 4.21-4.33%, the allowable error is weight percentage of 0-0.89%.

10. The method for manufacturing the polymer of claim 3, where the polymerizing step is performing a ring-opening metathesis polymerization (ROMP).

11. The method for manufacturing the polymer of claim 10, further comprising a step of: providing a ruthenium metal catalyst for the ring-opening metathesis polymerization.

12. The method for manufacturing the polymer of claim 10, further comprising a step of: providing ethyl vinyl ether for terminating the ring-opening metathesis polymerization.

13. The method for manufacturing the polymer of claim 10, wherein the pyrene-containing norbornene methylene amine polymer is dissolved in tetrahydrofuran(THF), and precipitated in methanol for purification.

* * * * *